United States Patent
Owings et al.

(10) Patent No.: US 10,930,375 B2
(45) Date of Patent: Feb. 23, 2021

(54) FACILITATING MODIFYING REFERENCE LABORATORIES

(75) Inventors: Ryan C. Owings, Kansas City, MO (US); Nneka Amarachi Dawn Oji, Kansas City, MO (US)

(73) Assignee: CERNER INNOVATION, INC., Overland Park, KS (US)

( * ) Notice: Subject to any disclaimer, the term of this patent is extended or adjusted under 35 U.S.C. 154(b) by 0 days.

(21) Appl. No.: 13/341,458

(22) Filed: Dec. 30, 2011

(65) Prior Publication Data
US 2013/0173289 A1    Jul. 4, 2013

(51) Int. Cl.
*G16H 10/40*    (2018.01)

(52) U.S. Cl.
CPC ................... *G16H 10/40* (2018.01)

(58) Field of Classification Search
CPC ......... G06Q 50/22; G06Q 50/24; G16H 10/40
See application file for complete search history.

(56) References Cited

U.S. PATENT DOCUMENTS

| | | |
|---|---|---|
| 7,363,240 B1 | 4/2008 | Armentano et al. |
| 7,392,237 B2 | 6/2008 | Pratt |
| 7,610,192 B1 | 10/2009 | Jamieson |
| 2002/0032583 A1 | 3/2002 | Joao |
| 2002/0083075 A1 | 6/2002 | Brummel et al. |
| 2003/0110059 A1 | 6/2003 | Janas, III et al. |
| 2004/0083217 A1 | 4/2004 | Brackett et al. |
| 2004/0204910 A1 | 10/2004 | Brumbach et al. |
| 2004/0267562 A1 | 12/2004 | Fuhrer et al. |
| 2006/0287997 A1* | 12/2006 | Rugh ............. G06Q 30/02 |
| 2007/0055545 A1 | 3/2007 | Maughan et al. |
| 2007/0129894 A1 | 6/2007 | Yung et al. |
| 2007/0196909 A1 | 8/2007 | Showalter et al. |
| 2008/0015892 A1 | 1/2008 | Gowdy et al. |
| 2009/0112882 A1 | 4/2009 | Maresh et al. |

(Continued)

FOREIGN PATENT DOCUMENTS

| | | |
|---|---|---|
| WO | 2008014117 A2 | 1/2008 |
| WO | 2010/126797 A1 | 11/2010 |

OTHER PUBLICATIONS

College of American Pathologists. Nov. 2011. (http://www.cap.org/...tentViewer/show.do?printFriendly=true&contentReference=cap_today%2F1111%2F1111_newsbytes.html [Jun. 12, 2013 5:25:10 PM)].*

(Continued)

*Primary Examiner* — Robert A Sorey
*Assistant Examiner* — Kristine K Rapillo
(74) *Attorney, Agent, or Firm* — Shook, Hardy & Bacon L.L.P.

(57) ABSTRACT

Computerized systems, methods, and graphical user interfaces are provided to facilitate communication between physician offices and reference laboratories. A reference laboratory content manager provides a centralized conduit for interfacing clients placing orders for reference laboratory testing and reference laboratories performing testing. The reference laboratory content manager leverages centralized mapping across organizations by managing associations for procedures between reference laboratory aliases and client aliases. The centralized mapping enables the reference laboratory content manager to manage updates from reference laboratories and facilitate clients wishing to modify utilization of reference laboratories.

17 Claims, 9 Drawing Sheets

900

| UPDATES | NEW | INACTIVATED |

BELOW IS A LIST OF THE PROCEDURES THAT YOU ARE USING AND HAVE BEEN UPDATED BY THE REF LAB.

| ╭910 | ╭920 | ╭930 | ╭940 | ╭950 |
|---|---|---|---|---|
| CODE | DESCRIPTION | MODIFICATION | COMPLETE | DISCARD |
| 12345 | COMPLETE BLOOD COUNT | REF RANG UPDATE | ☑ | ☐ |
| B4235 | LYTES | UPDATE METHODOLOGY | ☐ | ☑ |
| CDSEF | SODIUM LEVEL | UPDATED CONTAINER | ☑ | ☐ |
| BASIC | BASIC METABOLIC PANEL | UPDATED CONTAINER | ☑ | ☐ |

(56) References Cited

U.S. PATENT DOCUMENTS

| | | | |
|---|---|---|---|
| 2009/0144088 A1* | 6/2009 | Zubiller | G06Q 30/0283 |
| | | | 705/3 |
| 2010/0094649 A1 | 4/2010 | White | |
| 2010/0127067 A1 | 5/2010 | Eisenberg et al. | |
| 2010/0179820 A1 | 7/2010 | Harrison et al. | |
| 2011/0173021 A1* | 7/2011 | Houriet, Jr. | G06Q 50/22 |
| | | | 705/2 |
| 2011/0246224 A1 | 10/2011 | Green, III et al. | |
| 2012/0215481 A1 | 8/2012 | Covey et al. | |
| 2013/0132285 A1* | 5/2013 | Richards et al. | 705/300 |
| 2013/0173278 A1 | 7/2013 | Owings et al. | |
| 2013/0173290 A1 | 7/2013 | Owings et al. | |

OTHER PUBLICATIONS

First Action Interview Pre-Interview Communication dated Jun. 3, 2013 regarding U.S. Appl. No. 13/341,469, 4 pages.
Final Office Action dated Dec. 13, 2013 regarding U.S. Appl. No. 13/341,469, 29 pages.
Final Office Action dated Jan. 5, 2015 in U.S. Appl. No. 13/341,469, 29 pages.
Non-Final Office Action dated Apr. 9, 2015 in U.S. Appl. No. 13/341,469, 29 pages.
Final Office Action dated Apr. 23, 2015 in U.S. Appl. No. 13/341,452, 11 pages.
First Action Interview Office Action dated Mar. 19, 2014 regarding U.S. Appl. No. 13/341,452 4 pages.
Non-Final Office Action dated Jul. 24, 2014 in U.S. Appl. No. 13/341,469, 23 pages.
Non-Final Office Action dated Sep. 12, 2014 in U.S. Appl. No. 13/341,452, 10 pages.
First Action Interview Office Action dated Aug. 5, 2013 in U.S. Appl. No. 13/341,469; 6 pages.
Preinterview First Action Interview dated Sep. 25, 2013 in U.S. Appl. No. 13/341,452; 10 pages.
Non-Final Office Action dated Oct. 7, 2015 in U.S. Appl. No. 13/341,452, 12 pages.
Final Office Action dated Oct. 16, 2015 in U.S. Appl. No. 13/341,469, 31 pages.
Non-Final Office Action dated Oct. 7, 2016 in U.S. Appl. No. 13/341,452, 11 pages.
Non-Final Office Action dated Nov. 1, 2016 in U.S. Appl. No. 13/341,469, 32 pages.
Final Office Action dated May 5, 2016 in U.S. Appl. No. 13/341,452, 12 pages.
Final Office Action dated Jun. 28, 2017 in U.S. Appl. No. 13/341,469, 34 pages.
Final Office Action dated Jul. 17, 2017 in U.S. Appl. No. 13/341,452, 19 pages.
Non-Final Office Action dated Feb. 16, 2018 in U.S. Appl. No. 13/341,469, 32 pages.
Non-Final Office Actions dated Mar. 22, 2018 in U.S. Appl. No. 13/341,452, 13 pages.
Cimino et al., "Automated Translation Between Medical Terminologies Using Semantic Definitions", M. D. Computing, vol. 7, No. 2, 1990, pp. 104-109.
Final Office Action received for U.S. Appl. No. 13/341,452, dated Dec. 5, 2018, 14 pages.
Final Office Action received for U.S. Appl. No. 13/341,469, dated Dec. 20, 2018, 20 pages.
Notice of Allowance received for U.S. Appl. No. 13/341,469, dated Jun. 27, 2019, 21 pages.
Wojcik, Barbara E, "The Challenge of Mapping between Two Medical Coding Systems", Military Medicine, 171, 11:1128, 2006, 9 pages.
Non-Final Office Action received for U.S. Appl. No. 13/341,452, dated Nov. 5, 2019, 9 pages.
Final Office Action received for U.S. Appl. No. 13/341,452, dated Apr. 15, 2020, 9 pages.
First Action Interview Pre-Interview Communication dated Jun. 19, 2013 in U.S. Appl. No. 13/341,458, 4 pages.
Advisory Action received for U.S. Appl. No. 13/341,452, dated Jul. 28, 2020, 5 pages.
Notice of Allowance received for U.S. Appl. No. 13/341,452, dated Dec. 28, 2020, 9 pages.
Nelson et al., "LabKey Server: An open source platform for scientific data integration, analysis and collaboration", BMC Bioinformatics, vol. 12, No. 71, Mar. 9, 2011, pp. 1-23.

* cited by examiner

REFERENCE LAB NETWORK

REFERENCE LAB PROCEDURE SEARCH

| * REFERENCE LAB: | LABCORP ▼ | * PROCEDURE NAME OR NETWORK ID: | SODIUM | SEARCH |

| PROCEDURE NETWORK ID | PROCEDURE NAME |
|---|---|
| 62604 | SODIUM, SERUM |
| 62647 | SODIUM, URINE |
| 62724 | SODIUM, URINE |

WELCOME: BUILD-TOOLS | LOGOUT |
MAPPING  CONNECTIONS  REPORTS

FIG. 6

REFERENCE LAB NETWORK

WELCOME: BUILD-TOOLS | LOGOUT |
MAPPING  CONNECTIONS  REPORTS

REFERENCE LAB PROCEDURE DETAILS

PROCEDURE SUMMARY | PROCEDURE ATTRIBUTES | PROCEDURE RESULTS

REFERENCE LAB PROCEDURE SEARCH —— REFERENCE LAB PROCEDURE DETAILS

PROCEDURE ATTRIBUTE

| | |
|---|---|
| METHOD | ION-SELECTIVE ELECTRODE (ISE); FLAME PHOTOMETER |
| MINIMUM VOLUME | 0.5 mL |
| SPECIMEN COLLECTION | SEPARATE SERUM FROM CELLS WITHIN 45 MINUTES OF VENIPUNCTURE. LABEL SPECIMEN AS SERUM |
| SPECIMEN CONTAINER | GEL-BARRIER TUBE OR RED-TOP TUBE |
| SPECIMEN STORAGE | MAINTAIN SPECIMEN AT ROOM TEMPERATURE |
| SPECIMEN TYPE | SERUM |
| SPECIMEN VOLUME | 1 mL |
| SPECIAL INSTRUCTIONS | |
| TESTING FREQUENCY | SET UP & REPORTED SUNDAY THRU FRIDAY ON ALL SHIFTS |

WELCOME, RYAN! HOME SIGN OUT

OVERVIEW | HEALTH RECORD | CONNECTIONS | SETTINGS

RYAN OWINGS

⇨ SHARE THIS RECORD
+ ADD A PERSON
+ PLACE LAB ORDER

PLACING LAB ORDER                                  SHARE THIS RECORD

REFERENCE LAB PROCEDURE SEARCH — 805

* PROCEDURE NAME OR NETWORK ID:  CBC   [SEARCH]

PROCEDURE NETWORK ID           PROCEDURE NAME
60406                          CBC WITH DIFFERENTIAL/PLATELET

810 —                    820 —                    830 —

LAB A                    LAB B                    LAB C

PRICE: $40               PRICE: $45               PRICE: $30
TAT: 2 DAYS              TAT: 2 DAYS              TAT: 1 DAY
RATING: 3 STARS          RATING: 1 STAR           RATING: 5 STARS

[PLACE ORDER]            [PLACE ORDER]            [PLACE ORDER]

FIG. 9

| UPDATES | NEW | INACTIVATED | | | |
|---|---|---|---|---|---|

BELOW IS A LIST OF THE PROCEDURES THAT YOU ARE USING AND HAVE BEEN UPDATED BY THE REF LAB.

| CODE (910) | DESCRIPTION (920) | MODIFICATION (930) | COMPLETE (940) | DISCARD (950) |
|---|---|---|---|---|
| 12345 | COMPLETE BLOOD COUNT | REF RANG UPDATE | ☑ | ☐ |
| B4235 | LYTES | UPDATE METHODOLOGY | ☐ | ☑ |
| CDSEF | SODIUM LEVEL | UPDATED CONTAINER | ☑ | ☐ |
| BASIC | BASIC METABOLIC PANEL | UPDATED CONTAINER | ☑ | ☐ |

900

FACILITATING MODIFYING REFERENCE LABORATORIES

CROSS REFERENCE TO RELATED APPLICATIONS

This application is related to commonly assigned U.S. patent applications entitled "Managing Updates from Reference Laboratories" and "Leveraging Centralized Mapping Between Organizations" filed concurrently herewith on the same date.

BACKGROUND

Clinical reference laboratory testing plays a key role in many facets of the healthcare process. Many of the decisions made by healthcare providers regarding patient care, from initial diagnosis through treatment and ultimate prognosis, are dictated by reference laboratory testing. For example, approximately 80% of all diagnoses are associated with a reference laboratory test. Given the crucial and prevalent role of clinical reference laboratory testing in the medical arena, it is imperative that the reference laboratory testing process provide results to healthcare providers in a timely and efficient manner.

While reference laboratory testing may sometimes be performed at the point-of-care, such as at a physician office or hospital, in many cases, the reference laboratory located at the same facility as the point-of-care may not be capable of performing a type of test required or the point-of-care location may not maintain a reference laboratory. In such cases, physical specimens collected from patients must be sent to a distant reference laboratory for testing. Currently, requesting clinical reference laboratory testing from distant reference laboratories and disseminating results are often part of a manual process, which is tedious, inefficient, and error prone. For example, in the context of a physician office requesting reference laboratory testing for a patient, it is often difficult for the physician office to determine an appropriate reference laboratory to perform the testing. Typically, the physician office will maintain information, such as the testing capabilities for each of a number of reference laboratories and records indicating the insurance each reference laboratory accepts. Accordingly, personnel at the physician office must manually review the information and determine an appropriate reference laboratory.

This approach is prone to errors, such as a physical specimen being sent to a reference laboratory that is incapable of performing the test requested and/or that does not accept the patient's insurance. In some cases, requests for reference laboratory testing may be ambiguous or incomplete from the perspective of the reference laboratory performing the testing. For example, if a reference laboratory receives a request to perform testing for hepatitis, the reference laboratory doesn't have sufficient information to know the specific type of hepatitis for which to test. Accordingly, the reference laboratory may perform the incorrect test. Alternatively, the reference laboratory may be required to contact the requesting party (e.g., by telephone) for clarification.

Further, current reporting and tracking of reference laboratory testing results is often not a seamless process. Results reporting is frequently a manual process, such as through mailing, faxing, emailing, or phoning results to the appropriate healthcare provider, providing opportunities for the miscommunication of results. If a healthcare provider does not receive results in a timely manner, the provider typically must call the reference laboratory to determine the status of the results. In cases in which the patient's results need to be reviewed and used for care at multiple healthcare providers, it is typically the burden of the patient to carry the results from institution to institution.

Currently, some larger reference laboratories provide proprietary software and/or hardware for entering orders for reference laboratory testing and for accessing results. In addition, some electronic medical record systems may interface with reference laboratories for order entry and result viewing. However, the software and/or hardware provided by each reference laboratory is specific to that particular reference laboratory. Likewise, for electronic medical record systems, individual interfaces are required for each reference laboratory.

Because individual interfaces are required for each reference laboratory, alias maps must be created for each reference laboratory. The alias maps provide an interface between how the physician office codes a particular test and how each reference laboratory codes the same test. Additional mapping must be provided to ensure a physician office receives the results it expects for the particular test. Attributes associated with each test provide guidance for the physician office acquiring a specimen. There is often variance between these attributes among reference laboratories even for the same test. Typically, a physician office utilizes a minimum of twenty to thirty reference laboratories to satisfy the needs of patients, insurance companies, and testing requirements. Unfortunately, reference laboratories frequently change the codes associated with a given test or type of measurement. Generally, reference laboratories send out code changes once a week, often in excess of two hundred changes a month. Each time a physician office receives the changes from each reference laboratory, a manual process is required to see how many of the code changes affect the physician office receiving the code changes. As a result, many physician offices simply resort to utilizing paper. Even when the physician offices employ an electronic means to interface with the laboratory software and/or hardware, the effort to maintain an accurate alias map for each reference laboratory is time consuming and costly because there is no centralized mapping that can be leveraged between organizations. Exacerbating this problem further is that it is equally time consuming and costly to change reference laboratories should the need arise because new alias maps need to be created each time a physician office changes or adds a reference laboratory.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to providing a reference laboratory network in a clinical computing environment to facilitate communication between physician offices and reference laboratories. Accordingly, in one aspect, an embodiment of the present invention is directed to a method that facilitates a method of leveraging centralized mapping between organizations. A selection of at least one reference laboratory and a selection of procedures to be provided by each at least one reference laboratory is received. A client order alias is received from a client for each selected procedure. A client results alias is received from a client for one or more expected results for each selected procedure. An order superset is built for each selected procedure containing an identification of a procedure mapped to the client order alias. A result superset is built for each procedure containing the identification of one or more expected results mapped to the client results alias.

In another aspect, an embodiment of the present invention is directed to a computer system for leveraging centralized mapping between organizations. The computer system comprises a processor coupled to a computer storage medium having stored thereon a plurality of computer software components executable by the processor. A laboratory alias component receives a laboratory order alias from at least one reference laboratory for each provided procedure and a laboratory results alias for one or more results expected from each provided procedure. A client alias component receives a client order alias from at least one client for each selected procedure and a client results alias for one or more expected results for each selected procedure. A superset component builds an order superset for each selected procedure containing a network identification of each procedure mapped to the client order alias and a result superset for each selected procedure containing a network identification of the one or more expected results mapped to the client results alias. A namespace component builds an order namespace for the at least one reference laboratory that includes the network identification of the procedure and the laboratory alias for each provided procedure and a result namespace for the at least one reference laboratory that includes the network identification of the one or more expected results and the laboratory results alias for each provided procedure.

In another aspect, an embodiment of the present invention is directed to a graphical user interface (GUI) to facilitate leveraging centralized mapping between organizations. A first display area is configured to display a search for identifying a procedure. A second display area is configured to display a list of possible procedures that are responsive to the search. A third display area is configured to display one or more of an identification of each reference laboratory capable of performing a selected procedure, a cost associated with the selected procedure for each reference laboratory, a turn-around-time associated with the selected procedure for each reference laboratory, and a rating for each reference laboratory.

In another aspect, an embodiment of the present invention is directed to a method that facilitates a method of modifying reference laboratories. A request from a client to modify at least one reference laboratory utilized by the client is received. A mapping associated with the at least one reference laboratory to reflect the modification is automatically updated for the client. The client is alerted that the at least one reference laboratory has been modified.

In another aspect, an embodiment of the present invention is directed to a computer system for modifying reference laboratories. The computer system comprises a processor coupled to a computer storage medium having stored thereon a plurality of computer software components executable by the processor. A modification component receives a request from a client to modify at least one reference laboratory utilized by the client. An automatic modification component automatically updates a mapping associated with the at least one reference laboratory to reflect the modification for the client. An activation component activates the modification and alerts the client that the at least one reference laboratory has been modified.

In another aspect, an embodiment of the present invention is directed to a graphical user interface (GUI) to facilitate modifying reference laboratories. A first display area is configured to display a list of available reference laboratories. A second display area is configured to display a list of available procedures. A third display area is configured to display procedure attributes.

In another aspect, an embodiment of the present invention is directed to a method that facilitates managing updates from reference laboratories. Updates are received from at least one reference laboratory. The updates from the at least one reference laboratory are mapped. The mapped updates are communicated to at least one client. The mapped updates are committed.

In another aspect, an embodiment of the present invention is directed to a computer system for managing updates from reference laboratories. The computer system comprises a processor coupled to a computer storage medium having stored thereon a plurality of computer software components executable by the processor. An update component receives updates from at least one reference laboratory. A mapping component maps the updates from the at least one reference lab. A communication component communicates the mapped updates to at least one client. A commit component commits the mapped updates.

In another aspect, an embodiment of the present invention is directed to a graphical user interface (GUI) to facilitate leveraging centralized mapping between organizations. A first display area is configured to display updates for at least one reference laboratory. A second display area is configured to display the mapping for the at least one reference laboratory. A third display area is configured to display committed updates.

BRIEF DESCRIPTION OF THE SEVERAL VIEWS OF THE DRAWINGS

The present invention is described in detail below with reference to the attached drawing figures, wherein:

FIG. 6 is an illustrative graphical user interface display of a reference laboratory procedure search in accordance with an embodiment of the present invention;

FIG. 7 is an illustrative graphical user interface display of procedure attributes in accordance with an embodiment of the present invention;

FIG. 8 is an illustrative graphical user interface display of placing a laboratory order in accordance with an embodiment of the present invention; and FIG. 9 is an illustrative graphical user interface display of procedure updates in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods, systems, and graphical user interfaces to facilitate leveraging centralized mapping between organizations. Embodiments of the present invention provide computerized methods, systems, and graphical user interfaces to facilitate modifying reference laboratories. Embodiments of the present invention provide computerized methods, systems, and graphical user interfaces to facilitate managing updates from reference laboratories. The reference laboratory network provides a centralized conduit for maintaining a mapping of one or more reference laboratories orders and results to facilitate entities (i.e., clients) utilizing reference laboratory testing (e.g., hospitals, physician offices, patients, etc.), reference laboratories performing the testing, and intended recipient of testing results. The mapping allows clients to easily build an interface with one or more reference laboratories and manage any necessary updates. The reference laboratory network further allows clients to easily modify one or more reference laboratories utilized by the client, such as may be necessary if the client desires to change, add, or remove a particular reference laboratory.

Figure 1:
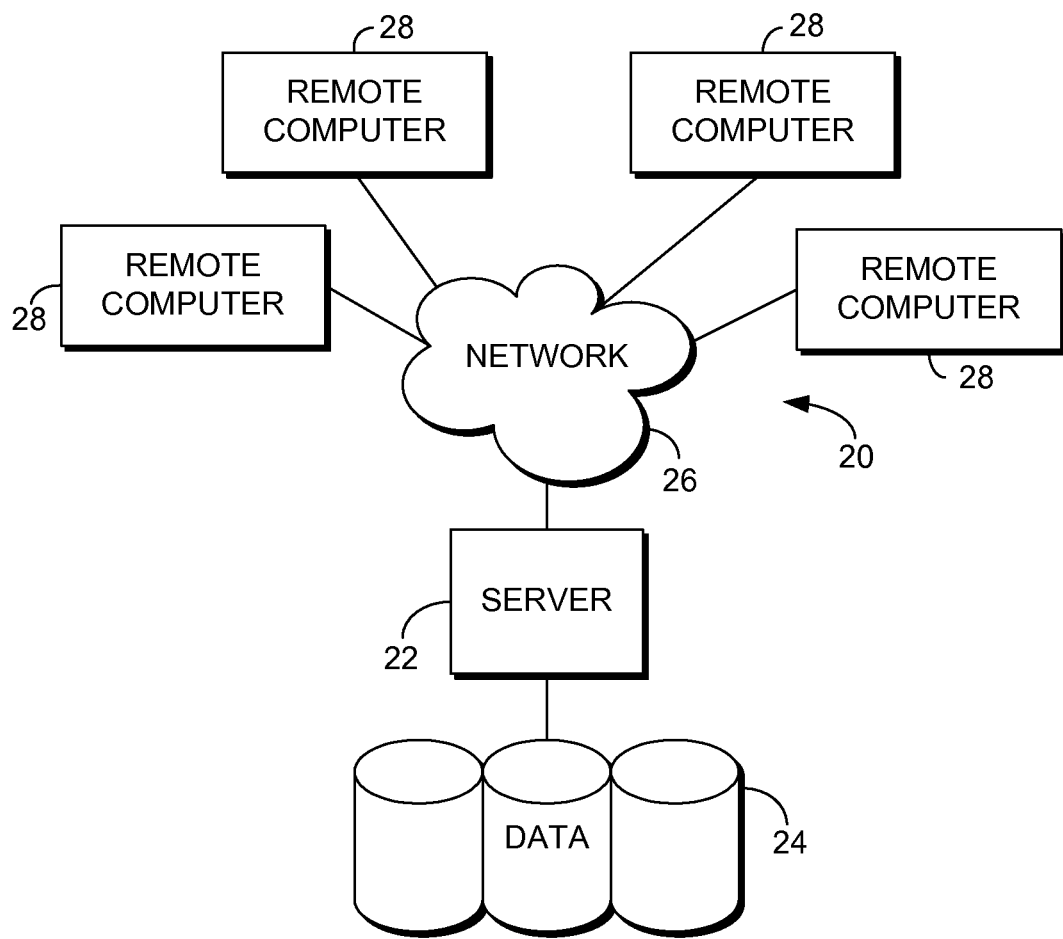
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (USA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical reference laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, reference laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
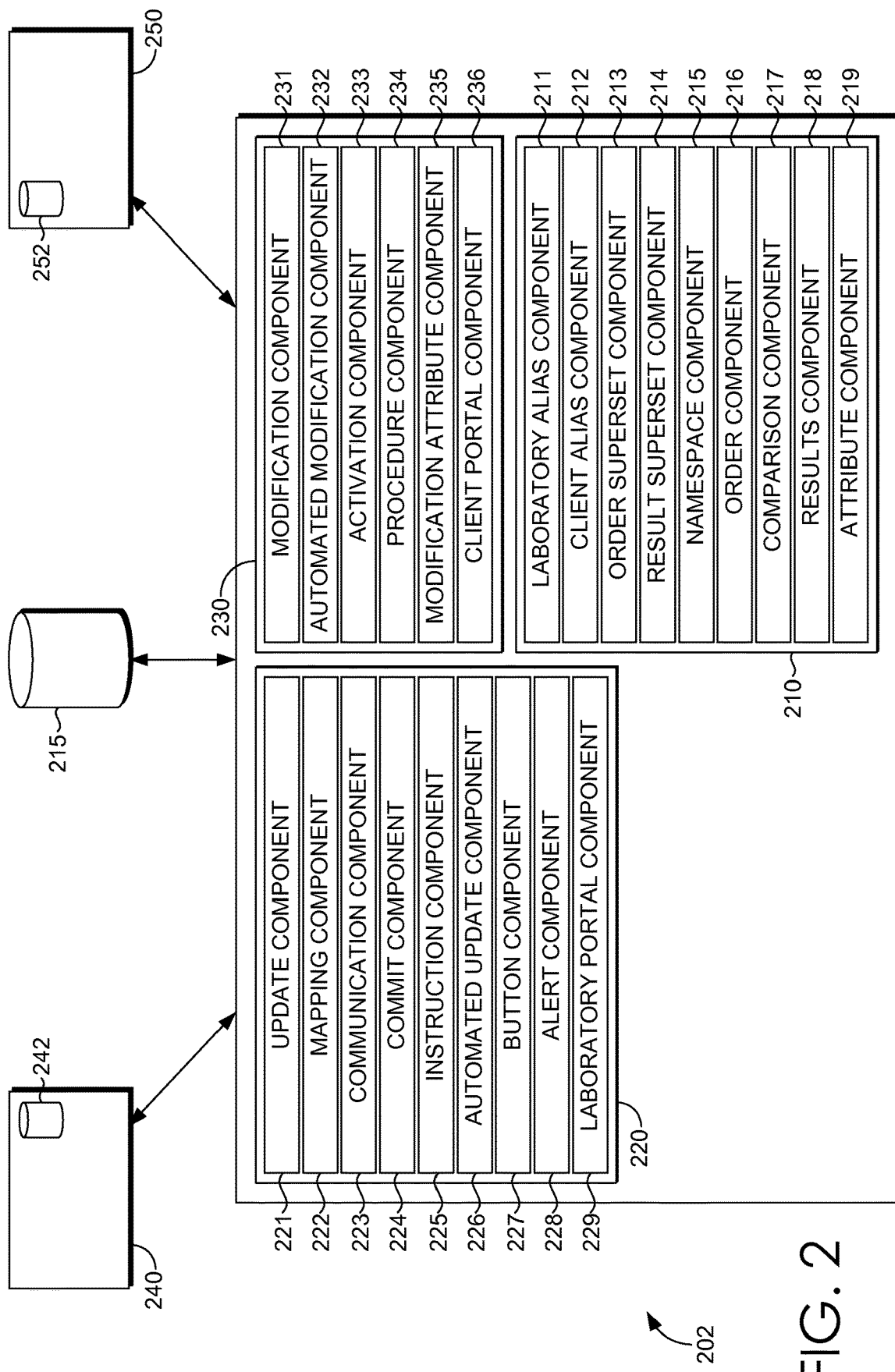
FIG. 2 is a block diagram showing an exemplary architecture for providing a reference laboratory network in accordance with an embodiment of the present invention.

Referring now to FIG. 2, a block diagram is provided illustrating an exemplary computing system architecture 200 for providing a reference laboratory network in accordance with embodiments of the present invention. It will be appreciated that the computing system architecture shown in FIG. 2 is merely an example of one suitable computing system and is not intended as having any dependency or requirement related to any single module/component or combination of modules/components.

As shown in FIG. 2, a reference laboratory content manager 202 may be provided to coordinate, among other things, communicating orders, results, and updates between clients and reference laboratories. The reference laboratory content manager 202 may act as a common interface or switch between and among multiple entities requesting reference laboratory testing and multiple reference laboratories performing the testing. As such, the reference laboratory content manager 202 serves as a conduit for communication of reference laboratory testing orders, results, and updates. Healthcare providers, such as hospitals, physician offices, and the like, may place orders for reference laboratory testing, track the status of testing, receive results, and otherwise communicate with appropriate reference laboratories via the reference laboratory content manager 202. In addition, reference laboratories may receive orders for reference laboratory testing and route the results to the appropriate recipients via the reference laboratory content manager 202. The reference laboratory content manager 202 manages the mapping between the codes utilized by reference laboratories and the codes utilized by clients, such that the clients do not have to be aware of or maintain the mapping. The reference laboratory content manager 202 manages receiving updates from the reference laboratories and determines which updates apply to which clients.

One or more databases, such as the database 215, may be associated with the reference laboratory content manager 202, for storing a variety of information to facilitate the mapping process. For example, the database 215 may maintain information regarding the types of testing available at each participating reference laboratory. In addition, the database 215 may maintain insurance provider information for eligibility and coverage purposes. The details and status of orders entered into the reference laboratory content manager 202 may also be maintained in the database 215. Further, the database 215 may maintain testing results and/or pointers to testing results stored at a reference laboratory's internal database 242. The database may further maintain client order aliases and client result aliases and/or pointers to such information stored at a client's internal database 252.

As shown in FIG. 2, the reference laboratory content manager 202 may be capable of communicating with a number of different entities, such as a reference laboratory 240 or a client 250 (e.g., physician office, hospital, and the like), for example, for modifying for a client the utilization of a reference laboratory, managing updates from a reference laboratory, or leveraging centralized mapping between organizations. It should be noted that the entities shown communicating with the reference laboratory content manager 202 in FIG. 2 are provided by way of example only and are not intended to limit the scope of the present invention in any way. For example, a variety of other types of entities may communicate with the reference laboratory content manager 202. In addition, although only a single reference laboratory 240 and client 250 are shown in FIG. 2, in operation, multiple hospitals, physician offices, draw stations, insurance providers, patients, and reference laboratories may communicate with the reference laboratory content manager 202.

Each entity may have a computing device, such as a remote computer 28 of FIG. 1, for communicating with the reference laboratory content manager 202. In addition, communication between the reference laboratory content manager 202 and the various entities may be via one or more networks, which may comprise one or more wide area networks (WANs) and one or more local area networks (LANs), as well as one or more public networks, such as the Internet, and one or more private networks. Further, entities may be able to access the reference laboratory content manager 202 in a variety of ways within the scope of the present invention. For example, in some embodiments, an entity may have a native clinical computing system, which may interface with and be able to communicate with the reference laboratory content manager 202. In other embodiments, a client application associated with the reference laboratory content manager 202 may reside on an entity's computing device facilitating communication with the reference laboratory content manager 202. In further embodiments, communication may simply be a web-based communication, using, for example, a web browser to access the reference laboratory content manager 202 via the Internet. Any and all such variations are contemplated to be within the scope of embodiments of the present invention.

In operation, an entity, such as the client 250, for example, may access the reference laboratory content manager 202 to enter an order for reference laboratory testing. In some cases, patients may wish to order his/her own reference laboratory testing and may access the reference laboratory content manager 202 to enter an order (e.g., via a home computer). An order comprises a request for reference laboratory testing to be performed and may include a variety of information, such as the type of reference laboratory testing requested, an identification of a physical specimen, the patient, the place of collection of a physical specimen, the time of collection of a physical specimen, insurance provider information, and intended recipients of reference laboratory testing results, for example.

An order for reference laboratory testing may be created by a user accessing the reference laboratory content manager 202 (e.g., remotely via a computing device communicating with the reference laboratory content manager 202) and entering the order. Typically, the order will be entered at the place the physical specimen (e.g., a blood sample, urine sample, throat swab, etc.) is collected. For example, a physician office that collects a physical specimen from a patient will typically enter the order. However, in some cases, an order may be entered from a location different from the place of collection. For example, a physician office may enter an order for a patient, while the specimen is collected from the patient at a draw station. Any and all such variations are contemplated to be within the scope of the present invention.

In some embodiments of the present invention, the reference laboratory content manager 202 may automatically select a reference laboratory based on information entered via an order. For instance, the reference laboratory content manager 202 may determine eligible reference laboratories based on the type of test requested and reference laboratory capability information maintained, for example, in database 215. In addition, the reference laboratory content manager may utilize insurance provider and eligibility information to place reference laboratory testing orders within a patient's insurance coverage. Insurance provider information may be stored by the reference laboratory content manager 202, for example, in the database 215. In some embodiments, the reference laboratory content manager 202 may communicate with insurance providers to access such information. Further, reference laboratory preferences may be established for users such that preferred reference laboratories are utilized if they are determined to be eligible. In another embodiment, the insurance eligibility may be determined prior to submission of the sample and performance of the test. A variety of other factors and data may be incorporated into the process of automatic reference laboratory selection by the reference laboratory content manager 202 within the scope of the present invention.

In further embodiments of the present invention, users may specify a particular reference laboratory for testing when entering an order. In such embodiments, the reference laboratory content manager 202 may be configured to determine whether a client-specified reference laboratory is an eligible reference laboratory based on factors, such as reference laboratory capabilities, insurance eligibility, and the like. In cases in which a specified reference laboratory is not an eligible reference laboratory, the reference laboratory content manager 202 may notify the client and provide an alternative reference laboratory.

Some types of testing and some reference laboratories necessitate unique specimen collection requirements. Accordingly, in some embodiments, the reference laboratory content manager 202 may maintain, for example in the database 215, unique specimen collection requirements. The reference laboratory content manager 202 may access and present any unique specimen collection requirements at the time of order placement based, for example, on the type of test requested and the selected reference laboratory.

The reference laboratory content manager 202 may further incorporate an identification system for identifying physical specimens and participating reference laboratories. For example, the reference laboratory content manager 202 may maintain or access barcode series for reference laboratories. In addition, the system may assign each physical specimen a unique identification code for facilitating the association of orders, physical specimens, and reference laboratory testing results. In some embodiments, clients may print requisitions and labels for physical specimens at the time of order entry.

The reference laboratory content manager 202 may maintain an account for each client entering orders and viewing results. By doing so the reference laboratory content manager 202 may group orders and results for each user. Accordingly, a user may be able to access the reference laboratory content manager 202 and view the status of pending orders and review testing results that have been entered. As such, the reference laboratory content manager 202 may provide one or more work queues to a user allowing the user to enter orders, track the status of pending orders, and review entered results.

After a physical specimen is collected from a patient, it may be routed to a selected reference laboratory, such as the reference laboratory 240, for testing. As indicated previously, the physical specimen may be identified by a variety of identification means, such as use of an identification number, barcode, or RFID tag, for example. Such identification allows the reference laboratory 240 to associate the physical specimen with the appropriate order. After receiving the physical specimen, the reference laboratory 240 performs the specified testing, thereby obtaining testing results for the patient. The reference laboratory 240 may then access the reference laboratory content manager 202 (e.g., via a computing device communicating with the reference laboratory content manager 202) and enter the results, associating the testing results with the appropriate order. In some cases, the reference laboratory 240 may maintain testing results in an associated database 242 and may provide a pointer to the results to the reference laboratory content manager 202, instead of providing the actual results.

The reference laboratory content manager 202 may provide a work queue to the reference laboratory 240, thereby allowing the reference laboratory 240 to perform a variety of activities with respect to reference laboratory testing result entry. For example, the work queue may allow the reference laboratory 240 to view orders that are pending testing results. In some embodiments, an alert may be provided if a testing result has not been entered for an order within a predetermined period of time. In addition, the work queue allows the reference laboratory 240 to enter testing results or result pointers and associate the testing results/pointers with orders.

After receiving reference laboratory testing results and/or pointers, the reference laboratory content manager 202 may store the results and/or pointers in an associated database, such as the database 215. Additionally, the reference laboratory content manager 202 allows recipients (e.g., those entities indicated in the order to receive the results) to view the reference laboratory testing results. Results may be communicated to recipients in a variety of ways within the scope of the present invention. For example, in some embodiments, the reference laboratory content manager 202 may first provide a notification to indicated recipients that reference laboratory testing results are available, and recipients may then access the results. The reference laboratory content manager may deliver such a notification to a recipient in any number of ways, such as, for example, via an electronic mail message, a message via a client application, a message via a recipient's native clinical computing system, or a generated voice recording. In some embodiments of the present invention, the reference laboratory content manager 202 may simply deliver the results and/or result pointers to the recipients. The delivery of results to recipients may be via any number of ways within the scope of the present invention, such as for example, an electronic mail message, a client application, a recipient's native clinical computing system, a generated voice recording, or via a fax machine.

In some embodiments of the present invention, the reference laboratory content manager 202 may communicate with an electronic medical record. As such, after receiving reference laboratory testing results, the reference laboratory content manager 202 may populate the testing results into the electronic medical record. By way of example only and not limitation, the electronic medical record may comprise a community health record or personal health record.

Referring again to FIG. 2, reference laboratory content manager 202 comprises a centralized mapping module 210, an updates module 220, and a modification module 230. Centralized mapping module 210 is responsible for leveraging centralized mapping between organizations. Updates module 220 is responsible for managing updates from reference laboratories. Modification module 230 is responsible for modifying reference laboratories.

Centralized mapping module 210 comprises laboratory alias component 211, client alias component 212, order superset component 213, result superset component 214, and namespace component 215. In various embodiments, centralized mapping module 210 includes order component 216, comparison component 217, results component 218, attribute component 219, and state reportable component (not shown in FIG. 2).

Laboratory alias component 211 receives a laboratory order alias from at least one reference laboratory for each provided procedure and a laboratory results alias for one or more results expected from each provided procedure. For example, each reference laboratory connected to the reference laboratory content manager 202 may provide particular tests (tests, procedures, orders). Each reference laboratory may have a unique coding system already in place for each provided test. Further, each reference laboratory may have a unique set of results associated with each provided test. The laboratory alias component 211 collects this information from all connected reference laboratories.

Client alias component 212 receives a client order alias from at least one client for each selected procedure and a client results alias for one or more expected results for each selected procedure. In one embodiment, the client alias component presents a list of selectable client order aliases to the client. The client selects the desired procedures according to their respective client order aliases and the client alias component assigns the client results aliases based on the selection of their corresponding client order aliases. In another embodiment, the client alias component presents a list of selectable procedures to the client and upon a selection of a particular procedure, the client identifies a client order alias and a client results alias that the client alias component retains. In one embodiment, the client only selects the procedures and the client order aliases and the client results aliases are automatically assigned, without receiving aliases from the client. For example, the network identification (discussed below) for the order superset and the results superset may be used as the client order alias and client results alias, respectively.

Order superset component 213 builds an order superset for each selected procedure containing a network identification of a procedure mapped to the client order alias. The mapping is an association between the network identification, or the particular procedure selected by the client, and the client order alias. As noted above, in one embodiment, the client order alias is automatically assigned by the client alias component when a procedure is selected by the client. The client order alias may be the network identification itself, or it may be a standardized display name that may easily identify the order. In this example, Result superset component 214 builds a result superset for each selected procedure containing a network identification of the one or more expected results mapped to the client results alias. The mapping is an association between the network identification for the expected results and the client results alias. As noted above, in one embodiment, the client results alias is automatically assigned by the client alias component when a procedure is selected by the client. The client results alias may be the network identification itself of the one or more expected results, or it may be a standardized display name that may easily identify the one or more expected results.

Namespace component 215 builds an order namespace for the at least one reference laboratory that includes the network identification of the procedure and the laboratory alias for each provided procedure and a result namespace for the at least one reference laboratory that includes the network identification of the one or more expected results and the laboratory results alias for each provided procedure. Thus, like the result superset component, the namespace component builds a mapping. The mapping for the order namespace provides an association between the network identification of the procedures and the laboratory alias. The mapping for the result namespace provides an association between the network identification for the one or more expected results and the laboratory results alias. As can be appreciated, any changes or modifications that need to be made on either the client side or the reference laboratory side can be managed by the reference laboratory content manager 202 because the reference laboratory content manager 202 coordinates and manages the mapping between all parties.

In one embodiment, order component 216 receives an order from client 240 for a test. In one embodiment, comparison component 217 provides the client with a comparison between one or more reference laboratories of one or more of a cost, a turn-around-time, and a rating. This information allows the client, or the patient, to select the desired reference laboratory based on the comparison. The order is typically identified by the client with its client order alias. The order component passes this information along to superset order component 213. Superset order component 213 identifies the network identification mapped to the client order alias and passes this information along to namespace component 215. Namespace component 215 utilizes the network identification to identify the laboratory alias and passes the order in the form of the laboratory alias to the reference laboratory 240.

After completing the order, reference laboratory 240 sends the results with the laboratory results alias to reference laboratory content manager 202. Namespace component 215 determines the network identification of the one or more expected results based on the laboratory results alias. Namespace component 215 passes the results along to the result superset component 214 along with the network identification of the one or more expected results. Result superset component 214 determines the client results alias associated with the network identification of the one or more expected results. In one embodiment, attribute component 219 confirms that attributes associated with the results match expected attributes associated with the order. For example, a particular a client making an order may expect the particular order to return four separate items as results. Attribute component 219 confirms that the attributes associated with the result (i.e., four separate items) match expected attributes associated with the order. In one embodiment, results component 218 normalizes and presents results associated with the order to the client. In one embodiment, the results are presented with the network identification of the one or more expected results. In another embodiment, the results are presented with the client results alias as determined by result superset component 214. In another embodiment, state reportable component communicates the results in real-time to the appropriate party. For example, state or local laws may require that certain results need to be reported to a public health agency. State reportable component determines which results are subject to such laws and communicates the results in real-time to the required party.

Updates module 220 comprises update component 221, mapping component 222, communication component 223, and commit component 224. In various embodiments, updates module 220 includes instruction component 225, automated update component 226, button component 227, alert component 228, and portal laboratory component 229.

Update component 221 receives updates from at least one reference laboratory. The updates may include details regarding the collection of specimens, such as collection container or tube-type, volume to be collected, method of collection, updates to acceptable ranges for results, and the like.

Mapping component 222 maps the updates from the at least one reference laboratory. Mapping component 222 identifies clients associated with the at least one reference laboratory and determines whether the updates are relevant to each client. For example, an update may only affect a particular test. If a client is associated with the at least one reference laboratory, but does not utilize the particular test, then the update is not relevant to that client. However, if the client does utilized the particular test, the update is relevant to that client and mapping component 222 identifies particular items in the mapping or association between the client and the reference laboratory that need to be updated. For example, attributes associated with the test may need to be updated such that the client ordering the test needs to collect a different amount of specimen, or utilized a different type of container. Mapping component identifies such items.

Communication component 223 communicates the mapped updates to at least one client. The mapped updates may identify aliases used by the reference laboratory or the client, description of the test requiring the update, the modification to the test, whether the update has been completed or discarded, and the like. The mapped updates may be communicated electronically, such as by electronic mail, fax, or through an interface the client uses to access or utilize reference laboratory content manager 202.

Commit component 224 commits the mapped updates such that the updates are applied for use by the clients. For example, if the update from the reference laboratory indicated that for a particular test a 2.0 mL of a specimen needs to be collected using a red-top tube rather than 1.0 mL using a yellow-top tube, once the update is committed, attributes noting the new requirements, rather than the previous requirements, will be presented to the client ordering the particular test.

In one embodiment, instruction component 225 provides instructions for the at least one client to follow to commit the mapped updates. The instructions may allow the client to manually make the appropriate changes to the mapping between the reference laboratory submitting the updates and the client. These updates may alter any of the mappings or associations discussed herein. In one embodiment, automated update component 226 commits the mapped updates without requiring further action by the at least one client. In one embodiment, button component 227 provides an update button for the at least one client that, when selected, commits the mapped updates. This button allows the client to review the updates before committing them, without requiring manual action by the client. Both the instruction component 225 and the button component 227 allow the client to retain control of the change management process.

In one embodiment, alert component 228 alerts the at least one client when an update has been committed. This may be particularly useful to help the client maintain an accurate record of when updates were committed. In one embodiment, the communication component 223 further provides a list of committed updates to the at least one client. This list is also particularly useful to a client maintaining records associated with updates.

In one embodiment, laboratory portal component provides a web-based portal for access by the at least one reference laboratory or the at least one client. In one embodiment, the web-based portal is configured to receive the updates from the at least one reference laboratory and may further provide access to review mappings pertaining to the at least one reference laboratory and its associated clients. In another embodiment, the web-based portal is configured to receive a selection of the updates from the at least one client to be committed.

Modification module 230 comprises modification component 231, automated modification component 232, and activation component 233. In various embodiments, modification module 230 includes procedure component 234, modification attribute component 235, and client portal component 236.

Modification component 231 receives a request from a client to modify at least one reference laboratory utilized by the client. In one embodiment, the modification is to add a new reference laboratory to a mapping associated with the client. In another embodiment, the modification is to remove a reference laboratory from the mapping associated with the client. In another embodiment, the modification is to replace a reference laboratory with another reference laboratory and the associated mapping for the client. For example, a client may have a contract with a particular reference laboratory that is up for renewal. In many instances, it is extremely difficult to switch reference laboratories, most often due to time, labor, and cost, if the contract negotiation is not progressing satisfactorily. In another example, a client may have identified a test that is not currently fulfilled by any contracted reference laboratory and the client may need to add a new reference laboratory that can execute the test.

Automated modification component 232 automatically updates, for the client, a mapping associated with the at least one reference laboratory to reflect the modification. As already discussed, the mapping allows the reference laboratory content manager 202 to manage all connections between the clients and the reference laboratories such that the clients never have to learn how each reference laboratory codes a particular test or results, and the attributes associated therewith. As can be appreciated, automated modification component 232 removes the concerns associated with time, labor, and cost to add, remove, or replace reference laboratories because it automatically updates the mapping for the client.

Activation component 233 activates the modification and alerts the client that the at least one reference laboratory has been modified. Once the mapping has been properly added, removed, or switched between the reference laboratory and the client, the activation component essentially turns on the mapping so the client may begin placing and receiving orders with the reference laboratory.

In one embodiment, procedure component 234 receives a list of procedures from the client to include in the mapping. In one embodiment, procedure component 234 further presents a list of selectable procedures that are available for the at least one reference laboratory. This allows the client to select only the relevant procedures that the client wants to include in the mapping for a particular reference laboratory, rather than include every procedure the reference laboratory performs. For example, a pediatric client may not want to include procedures that are unrelated to its practice. The pediatric client can select only those procedures provided by the reference laboratory that it desires to include in the mapping. Thus, the procedure component allows the client to retain control of what is available in its interface to the reference laboratory content manager 202.

In one embodiment, modification attribute component 235 presents attributes associated with each procedure. This allows, for example, the client to select the appropriate procedure when several related procedures have attributes that indicate different sets of results are provided. In one embodiment, each procedure from the list of procedures includes result types. In another example, the client is able to select the appropriate procedure when several related procedures have attributes that indicate different methods of acquiring a specimen are utilized. In one embodiment, attributes include one or more of method, minimum volume, specimen collection, specimen container, specimen storage, specimen type, specimen volume, special instructions, and testing frequency.

In one embodiment, client portal component 235 presents a portal accessible by the client. The portal allows the client access to the reference laboratory content manager 202 to initiate modifications or review the mapping for the client and associated reference laboratories.

Figure 3:
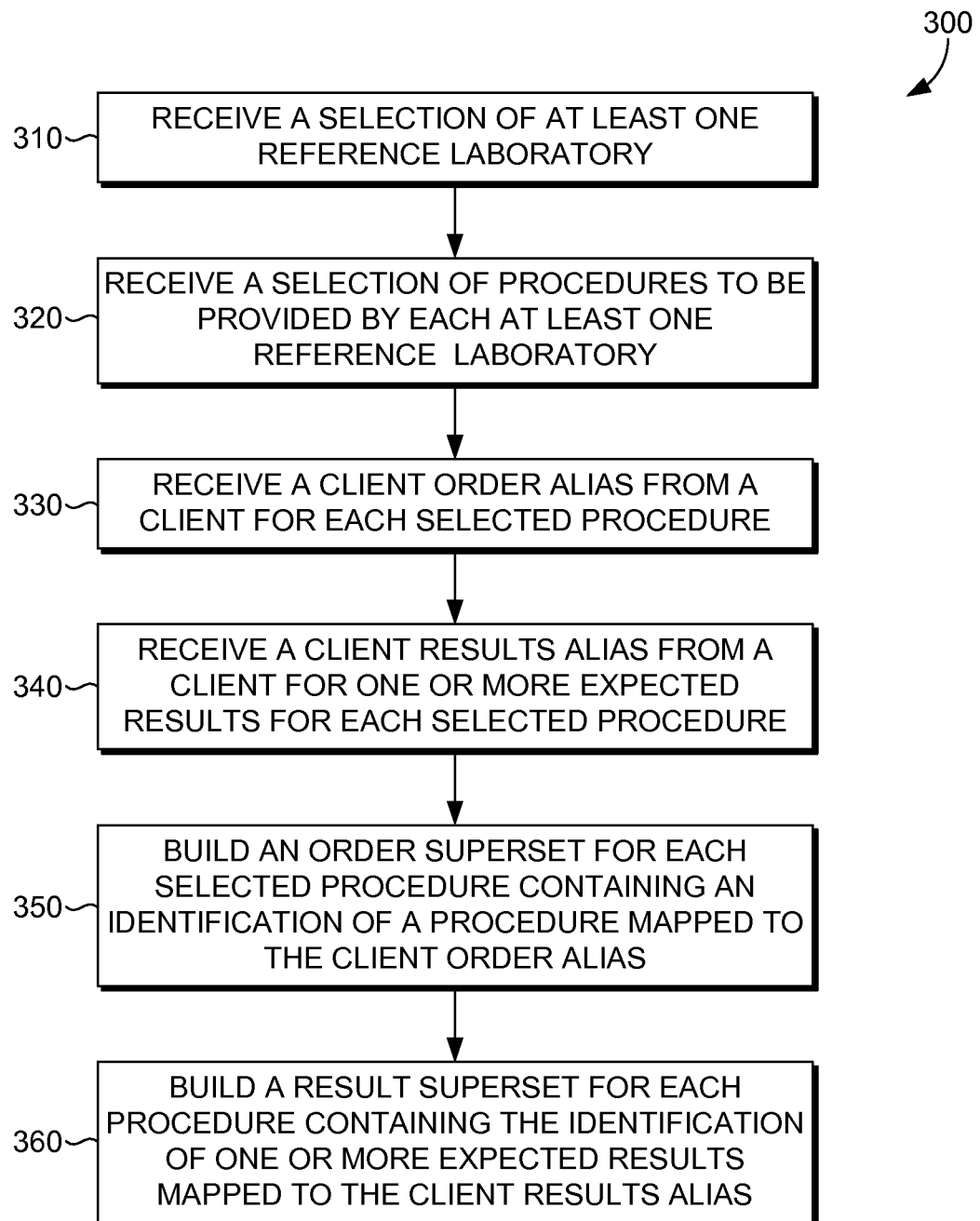
FIG. 3 is a flow diagram showing a method for leveraging centralized mapping between organizations in accordance with an embodiment of the present invention.

Turning now to FIG. 3, a flow diagram is provided illustrating a method 300 for leveraging centralized mapping between organizations in accordance with an embodiment of the present invention. Initially, as shown at step 310, a selection of at least one reference laboratory is received. For example, a physician office may have a contractual obligation to begin utilizing a new reference laboratory for particular tests. The physician office may access the reference laboratory content manager to set up the appropriate mapping for the particular tests for the new reference laboratory. Accordingly, at step 320 a selection of procedures to be provided by each at least one reference laboratory is provided.

At step 330, a client order alias from a client for each selected procedure is received. At step 340, a client results alias for one or more expected results for each selected procedure is received. In one embodiment, the client order alias and/or the client results alias is provided by the reference laboratory content manager. For example, the reference laboratory content manager may provide a search screen for the client to search for and identify tests (i.e., procedures) provided by the reference laboratory. When the client identifies the appropriate test in the search results, the reference laboratory content manager may provide an identification of the test such that, when the test is selected by the client, the identification is automatically utilized as the client order alias. Similarly, a client results alias may also be automatically provided by the reference laboratory content manager when the client selects the test. In another embodiment, the client order alias and/or the client results alias is provided by the client such that the client is able to maintain a naming convention utilized by that client.

At step 350, an order superset is built for each selected procedure containing an identification of a procedure mapped to the client order alias. The order superset provides an association between the client order alias and the identification of a test. As already mentioned, in one embodiment the client order alias is the identification of a test, as provided by the reference laboratory content manager. When the client order alias is provided by the client, such as when the client desires to utilize a proprietary naming convention, the reference laboratory content manager is able to track the utilization of the client with a standard internal naming convention (i.e., the identification provided by the reference laboratory content manager) for all clients. Such internal tracking allows the client to add, remove, or change (i.e., modify) reference laboratories with much less effort and cost because the reference laboratory content manager makes modifications to the mapping without requiring the client to go through the setup process again and identify particular tests.

Similarly, at step 360, a result superset is build for each procedure containing the identification of one or more expected results mapped to the client results alias. The result superset provides an association between the client results alias and the identification of one or more expected results for a particular test.

For example, a client may identify an electrolytes test as "Lytes". Thus, when the client searches the reference laboratory content manager for "Lytes", the reference laboratory content manager may return a list containing tests responsive to the search. Once the client selects the appropriate test, a client order alias is received. In one embodiment, the client enters "Lytes". The reference laboratory content manager may identify the selected test with the identification "123". Accordingly, the reference laboratory content manager builds the order superset and associates "Lytes" with "123". The identification "123" is utilized for every reference laboratory managed by the reference laboratory content manager, which allows the reference laboratory content manager to easily provide mapping for additional reference laboratories for the client.

Similarly, in one embodiment, the reference laboratory content manager maintains a Order-Results Relationship-Partner mapping and knows that the test "123" provided by the selected reference laboratory returns results for Na, K, Chl, and $CO_2$. The client may choose to identify these results with a client results alias. Accordingly, the reference laboratory content manager builds the result superset to associate sodium, potassium, chloride, and $CO_2$ with Na, K, Chl, and $CO_2$, respectively.

In one embodiment, a laboratory order alias is received for each procedure provided by each reference laboratory. Similar to the client order alias, the laboratory order alias allows each reference laboratory to maintain its own naming convention, or coding, for the procedures it provides. In one embodiment, a laboratory results alias for one or more results expected from each provided procedure is received from each reference laboratory. This allows the reference laboratory content manager to learn what types of results are expected for each provided procedure from each reference laboratory. This is important to manage consistency checking between the clients and the reference laboratories so that when a client makes an order, the client knows what type of results the order will yield, and when results are returned, the reference laboratory content manager knows if any results are missing and can immediately alert the reference laboratory.

In one embodiment, an order namespace for each at least one reference laboratory is built that includes the identification of the procedure and the laboratory order alias for each provided procedure. The order namespace is the mapping between the reference laboratories and the reference laboratory content manager and is utilized in conjunction with the order superset to determine the appropriate coding for the reference laboratory when the client enters an order.

In one embodiment, a result namespace for each at least one reference laboratory is built that includes an identification of the one or more expected results and the laboratory results alias for each provided procedure. The result namespace is the mapping between the reference laboratories and the reference laboratory content manager that is utilized in conjunction with the result superset to properly associate the results returned by the reference laboratory with the client placing the order.

In one embodiment, attributes associated with each provided procedure are received that provide context for the orders and/or results. For example, attributes may include one or more of method, minimum volume, specimen collection, specimen container, specimen storage, specimen type, specimen volume, special instructions, and testing frequency. In another example, attributes may include result types or units of measure. In one embodiment, attributes associated with the results are confirmed to match expected attributes to aid in the process of consistency checking, as discussed above. In one embodiment, the selected reference laboratory is alerts if the results do not match expected results.

In one embodiment, an order is received from the client for a procedure. In one embodiment, a list of available reference laboratories that can fulfill the order is provided. In one embodiment, the list includes one or more of an identification of each reference laboratory, a cost associate with the order for each reference laboratory, a turn-around-time associated with the order for each reference laboratory, and a rating for each reference laboratory. In one embodiment, one or more results associated with the order are received from the selected laboratory. In one embodiment, the results are normalized. In one embodiment, the normalized results are presented to the client.

Figure 4:
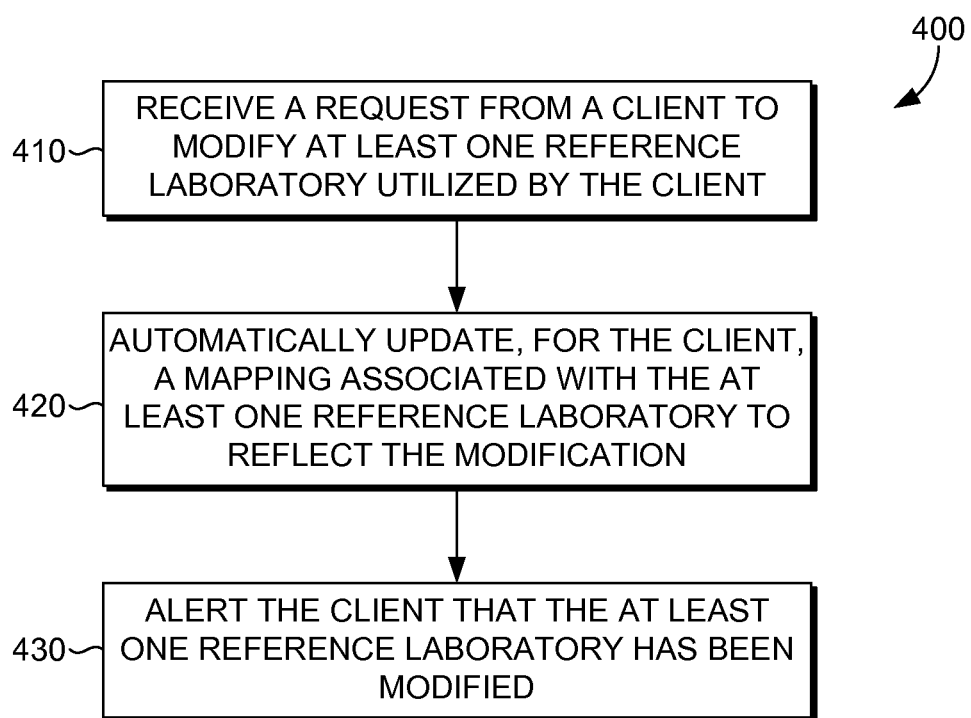
FIG. 4 is a flow diagram showing a method for facilitating modifying reference laboratories in accordance with an embodiment of the present invention.

Turning now to FIG. 4, a flow diagram is provided illustrating a method 400 for leveraging modifying reference laboratories, in accordance with an embodiment of the present invention. Initially, as shown at step 410, a request is received from a client to modify at least one reference laboratory utilized by the client. In one embodiment, the request comprises an identification of at least one dropped reference laboratory to drop for the client and at least one added reference laboratory to add for the at least one client. In another embodiment, the request comprises an identification of at least one added reference laboratory to add for the client. In another embodiment, the request comprises an identification of at least one dropped reference laboratory to drop for the client.

At step 420, a mapping associated with the at least one reference laboratory to reflect the modification is automatically updated for the client. In one embodiment, a list of procedures to include in the mapping is received from the client. In one embodiment, the list of procedures is selected from a list of available procedures for the at least one reference laboratory. For example, the client may be selecting a new reference laboratory to utilize for only certain procedures. Rather, than build a mapping for every procedure offered by the new reference laboratory, the client provides a list of or selects only those procedures that will be ordered at the new reference laboratory. At step 430, the client is alerted that the at least one reference laboratory has been modified.

In one embodiment, automatically updating a mapping associated with the at least one reference laboratory to reflect the modification comprises receiving a list of procedures from the client. Each procedure is mapped to a code associated with the at least one reference laboratory. As described in detail above, the code may represent the reference laboratory order or result alias and is associated with a network identification of the order or results. The network identification may be any standardized identification for that particular order or results. The network identification may then be associated with a client order or results alias to complete the base level order mapping between the client and the reference laboratory.

In one embodiment, the list of procedures is selected by the client via a web portal. In one embodiment, each procedure from the list of procedures includes attributes. In one embodiment, each procedure from the list of procedures further includes result types. In one embodiment, the attributes include one or more of method, minimum volume, specimen collection, specimen container, specimen storage, specimen type, specimen volume, special instructions, and testing frequency.

Figure 5:
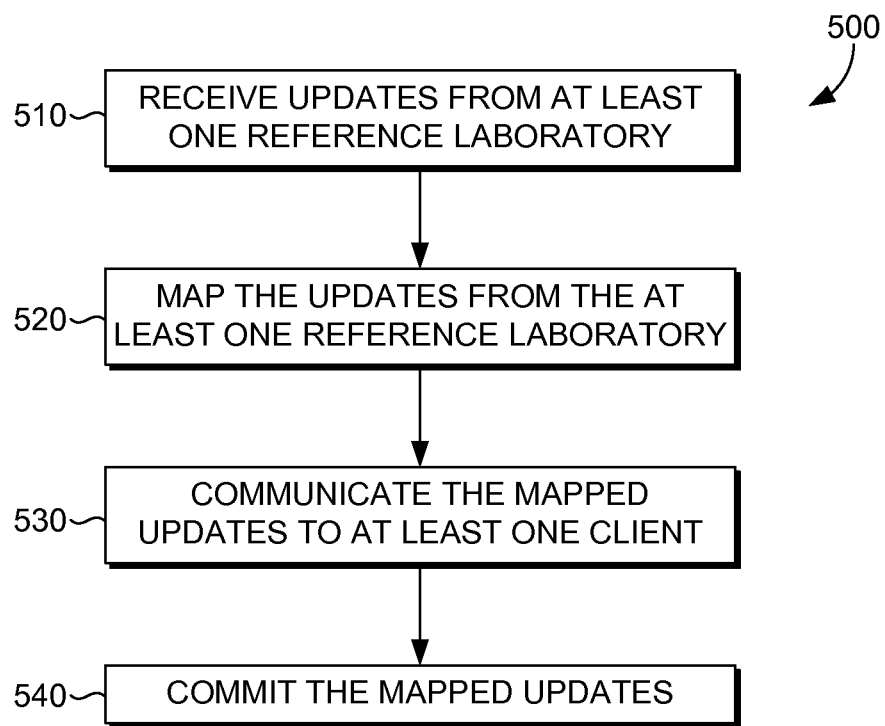
FIG. 5 is a flow diagram showing a method for managing updates from reference laboratories in accordance with an embodiment of the present invention.

Turning now to FIG. 5, a flow diagram is provided illustrating a method 500 for managing updates from reference laboratories, in accordance with an embodiment of the present invention. Initially, as shown at step 510, updates from at least one reference laboratory are received. The updates may be, for example, methodology updates, container updates, reference range updates, and the like. At step 520, updates from the at least one reference laboratory are mapped, as described above. The mapped updates are communicated to at least one client at step 530. The client may desire to see what updates are available and make a determination on whether to commit or discard the updates. At step 540, the mapped updates are committed.

In one embodiment, an update button is provided to the client. When the update button is selected, or activated, the mapped updates are committed. In another embodiment, instructions are provided for the client to follow to commit the mapped updates. For example, the client may desire to exert more control over how the updates are applied. Accordingly, the client manually commits the updates by following the provided instructions. In one embodiment, the client accesses the mapping via the portal and manually makes changes where appropriate to update the mapping. In this example, the client may have to manually adjust aliases, attributes, and the like. In one embodiment, the mapped updates are committed without requiring further action by the at least one client. In this example, the mapped updates are committed transparently to the client. In one embodiment, an alert is provided to the client when an update has been committed. In one embodiment, a list of committed updates is communicated to the client so the client is aware which updates have been committed.

In one embodiment, a web-based portal is provided for access by a reference laboratory or a client. In one embodiment, the web-based portal is configured to receive the updates from a reference laboratory. In one embodiment, the web-based portal is configured to receive a selection of updates from a client to be committed.

Referring now to FIG. 6, an illustrative screen display depicts a display of a reference laboratory procedure search 600, in accordance with embodiments of the present invention. A client desiring to order a particular procedure may first select the desired reference laboratory 610. A search for a procedure name (i.e., client order alias) or network identification is entered in the procedure search box 620. A set of responsive procedures 630 is returned including both the procedure network identification and the procedure name.

Referring now to FIG. 7, an illustrative screen display depicts a display of procedure attributes 700, in accordance with embodiments of the present invention. A list of procedure attributes 710 is provided to guide the client when sending a specimen to a particular reference laboratory for a particular procedure to meet the particular reference laboratories requirements to fulfill the particular procedure. For example, one or more of method, minimum volume, specimen collection, specimen container, specimen storage, specimen type, specimen volume, special instructions, and testing frequency are provided to the client.

Referring now to FIG. 8, an illustrative screen display depicts a display of placing a laboratory order 800, in accordance with embodiments of the present invention. A clinician desiring to order a particular procedure searches for the procedure in the search box 805. The clinician may utilize either the procedure name or the network identification of the procedure. Reference laboratories 810, 820, 830 providing the particular procedure are displayed. In various embodiments, the price, turn-around-time, and rating for each reference laboratory 810, 820, 830 are displayed so the client can place the order with an understanding of price, how long the test will take, and a rating of the reference laboratory. This information may be relayed to the patient so the patient can make an informed decision of which reference laboratory should perform the test.

Referring now to FIG. 9, an illustrative screen display depicts a display of procedure updates 900, in accordance with embodiments of the present invention. A client may view the procedure updates 900 to quickly and readily assimilate the updates for a particular reference laboratory that are applicable to the client. A code 910 identifies the reference laboratory order or results alias. A description 920 identifies the network identification, in one embodiment, and the client order or results alias, in another embodiment. The modification 930 identifies the update. The client may select to complete 940, or commit, or discard 950 the update.

As can be understood, embodiments of the present invention provide a centralized mechanism for networking entities wishing to order reference laboratory testing with reference laboratories capable of performing the testing. As such, embodiments of the present invention provide a conduit for the communication of reference laboratory testing orders, results, and updates. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. Non-transitory computer storage media having computer-executable instructions embodied thereon that, when executed by a computing system having a processor and a memory communicating through a computer network with a client computing device and at least one reference laboratory computing device, perform an improved method of modifying utilization of reference laboratories via a communication interface link through the computer network and utilizing a database for storing information to facilitate a mapping process, the method comprising:

providing, by the processor, a mapping associated with a current client of one or more reference laboratories, the mapping associating client aliases to reference laboratory aliases for the client;

receiving, by the processor, through the computer network, a request from the client computing device to modify the utilization of at least one reference laboratory included in the mapping associated with the client, wherein the request comprises an identification of one or more of: an added reference laboratory to add to the mapping, a dropped reference laboratory to remove from the mapping, and a replacement reference laboratory to replace with a different reference;

determining, by the processor, the reference laboratory aliases and the client aliases for a list of procedures;

determining, by the processor, from the reference laboratory aliases for the list of procedures, a network identification for each procedure of the list of procedures, wherein the network identification for each procedure is a standardized identification of that particular procedure;

automatically modifying, by the processor, the mapping by associating the network identification with the client alias for each procedure of the list of procedures to reflect the requested modification such that the modified mapping reflects the reference laboratory aliases of the identified one or more of the added reference laboratory, the dropped reference laboratory, and the replacement reference laboratory;

automatically modifying, by the processor, the communication interface link through the computer network between the client computing device and the at least one reference laboratory computing device based on the modified mapping;

electronically providing, by the processor, via the client computing device, an alert that the at least one reference laboratory has been modified;

activating the modification, by the processor, and providing a user interface via the client computing device that facilitates utilization of at least one reference laboratory via the client computing device based on the mapping; and wherein the client aliases and the mapping are specific to the client or the nature of the client and include at least one order alias and at least one expected results alias, wherein the at least one results alias is selected from different possible results aliases for a particular order alias, and wherein the mapping is confirmed by comparing an attribute of the at least one expected results alias to the attribute for the at least one order alias.

2. The media of claim 1, wherein the request from the client computing device to modify the at least one reference laboratory comprises the identification of at least one dropped reference laboratory and at least one added reference laboratory.

3. The media of claim 1, wherein the request from the client computing device to modify the at least one reference laboratory comprises the identification of at least one added reference laboratory.

4. The media of claim 1, further comprising receiving the list of procedures from the client computing device to include in the mapping.

5. The media of claim 4, wherein the list of procedures is selected from a list of available procedures for the at least one reference laboratory.

6. The media of claim 1, wherein automatically updating the mapping to reflect the modification comprises:
receiving the list of procedures from the client computing device; and
mapping each procedure from the list of procedures to a procedure code associated with the at least one reference laboratory, wherein the procedure code comprises an identifier for each procedure.

7. The media of claim 6, wherein the list of procedures is selected by the client computing device via a web portal.

8. The media of claim 7, wherein each procedure from the list of procedures includes attributes.

9. The media of claim 8, wherein each procedure from the list of procedures further includes result types.

10. The media of claim 8, wherein the attributes include one or more of method, minimum volume, specimen collection, specimen container, specimen storage, specimen type, specimen volume, special instructions, and testing frequency.

11. A computer system utilizing a database for storing information to facilitate a mapping process and facilitating modifying utilization of reference laboratories via a communication interface link through the computer network, the computer system comprising a processor communicating through the computer network with a client computing device and at least one reference laboratory computing device and coupled to a computer storage medium, the computer storage medium having stored thereon a plurality of computer software components executable by the processor, the plurality of computer software components comprising:

a centralized mapping module for mapping client aliases to reference laboratory aliases for an existing client of one or more reference laboratories, yielding a mapping associated with the client;

a modification component for receiving a request from the client computing device to modify at least one reference laboratory included in the mapping associated with the client, wherein the request comprises an identification of at least one of: an added reference laboratory to add to the mapping, a dropped reference laboratory to remove from the mapping, and a replacement reference laboratory to replace with a different reference laboratory;

an automatic modification component for: (1) determining the reference laboratory aliases and the client aliases for a list of procedures, and a network identification for each procedure of the list of procedures from the reference laboratory aliases for the list of procedures, wherein the network identification for each procedure is a standardized identification of that particular procedure; (2) automatically modifying the mapping by associating the network identification with the client alias for each procedure of the list of procedures to reflect the requested modification based on the requested modification, such that the modified mapping reflects the identified one or more of the added reference laboratory, the dropped reference laboratory, and the replacement reference laboratory; and (3) automatically modifying the communication interface link through the computer network between the client computing device and the at least one reference laboratory computing device based on the modified mapping;

an activation component for activating the modification and electronically providing an alert via the client computing device that the at least one reference laboratory has been modified and providing a user interface via the client computing device that facilitate utilization of at least one reference laboratory via the client computing device based on the mapping;

wherein the client aliases and the mapping are specific to the client or the nature of the client and include at least one order alias and at least one expected results alias, wherein the at least one results alias is selected from different possible results aliases for a particular order alias; and an attribute component for confirming that at least one attribute of the at least one expected results alias matches the at least one attribute for the at least one order alias.

12. The system of claim 11, further comprising a procedure component for receiving the list of procedures from the client computing device to include in the mapping.

13. The system of claim 12, wherein the procedure component further presents a list of selectable procedures that are available for the at least one reference laboratory.

14. The system of claim 12, further comprising an attribute component for presenting attributes associated with each procedure.

15. The system of claim 14, wherein each procedure from the list of procedures includes result types.

16. The system of claim 14, wherein the attributes include one or more of method, minimum volume, specimen collection, specimen container, specimen storage, specimen type, specimen volume, special instructions, and testing frequency.

17. The system of claim 11, further comprising a client portal component for presenting a portal accessible by the client computing device.

* * * * *

UNITED STATES PATENT AND TRADEMARK OFFICE
CERTIFICATE OF CORRECTION

PATENT NO. : 10,930,375 B2
APPLICATION NO. : 13/341458
DATED : February 23, 2021
INVENTOR(S) : Ryan C. Owings et al.

Page 1 of 1

It is certified that error appears in the above-identified patent and that said Letters Patent is hereby corrected as shown below:

In the Specification

Column 06, Line 18: Please remove "(USA)" and replace with --(ISA)--.

Column 12, Line 31: Please remove "In this example,".

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*